US011021950B2

(12) United States Patent
Siu et al.

(10) Patent No.: US 11,021,950 B2
(45) Date of Patent: Jun. 1, 2021

(54) PRODUCTION-LOGGING SENSOR

(71) Applicant: Probe Technology Services, Inc., Fort Worth, TX (US)

(72) Inventors: Kee Siu, Calgary (CA); Mark Lloyd, Calgary (CA); Johnathan Miko, Calgary (CA); Angel Mendoza, Calgary (CA)

(73) Assignee: Probe Technology Services, Inc., Fort Worth, TX (US)

( * ) Notice: Subject to any disclaimer, the term of this patent is extended or adjusted under 35 U.S.C. 154(b) by 39 days.

(21) Appl. No.: 16/432,953

(22) Filed: Jun. 6, 2019

(65) Prior Publication Data

US 2020/0386099 A1    Dec. 10, 2020

(51) Int. Cl.
| | |
|---|---|
| *G01V 3/18* | (2006.01) |
| *E21B 49/08* | (2006.01) |
| *G01V 3/20* | (2006.01) |
| *G01N 27/22* | (2006.01) |
| *G01N 27/07* | (2006.01) |
| *E21B 47/07* | (2012.01) |
| *G01N 33/28* | (2006.01) |
| *G01N 27/06* | (2006.01) |

(Continued)

(52) U.S. Cl.
CPC .............. *E21B 49/08* (2013.01); *E21B 47/07* (2020.05); *G01N 27/026* (2013.01); *G01N 27/06* (2013.01); *G01N 27/07* (2013.01); *G01N 27/226* (2013.01); *G01N 27/74* (2013.01); *G01N 33/2823* (2013.01); *G01V 3/20* (2013.01); *E21B 49/0875* (2020.05); *G01V 3/18* (2013.01); *G01V 3/30* (2013.01); *G01V 3/38* (2013.01)

(58) Field of Classification Search
CPC .. G01N 33/2823; G01N 27/06; G01N 27/026; G01N 27/74; G01N 27/07; G01N 27/226; G01V 3/20; G01V 3/18; G01V 3/38; G01V 3/30; E21B 49/08; E21B 47/07; E21B 49/0875
USPC ................ 324/323, 324, 376, 438
See application file for complete search history.

(56) References Cited

U.S. PATENT DOCUMENTS

| 5,736,637 A | 4/1998 | Evans et al. |
| 6,532,824 B1 | 3/2003 | Ueno et al. |

(Continued)

FOREIGN PATENT DOCUMENTS

WO    WO2009091907    7/2009

OTHER PUBLICATIONS

PCT/US20/34566 International Search Report dated Aug. 12, 2020.

*Primary Examiner* — Raul J Rios Russo
(74) *Attorney, Agent, or Firm* — D. Tiller Law PLLC; Donald Tiller

(57) ABSTRACT

A sensor comprising three electrodes forming two electrode pairs, each pair having a gap between the electrodes, is disclosed. An electrically insulating layer is disposed in the gap of one electrode pair. The sensor may include a RC oscillator circuit connected to the electrode pair having the insulating layer such that the electrode pair contributes to the capacitance of the circuit. The sensor may include a power supply connected to the other electrode pair to provide a voltage across and current through material in the pair's gap. The sensor may be disposed in a borehole to allow borehole fluid to enter the gaps and the RC oscillator circuit and power supply may be operated to provide a measure of capacitance and resistance characteristics of the borehole fluid.

14 Claims, 5 Drawing Sheets

(51) Int. Cl.
  *G01N 27/02* (2006.01)
  *G01N 27/74* (2006.01)
  *G01V 3/38* (2006.01)
  *G01V 3/30* (2006.01)

(56) References Cited

U.S. PATENT DOCUMENTS

| | | |
|---|---|---|
| 7,119,551 B2 | 10/2006 | Burdick |
| 7,489,144 B2 | 2/2009 | Hetherington et al. |
| 8,433,255 B2 | 4/2013 | Harnishfeger |
| 8,538,701 B2 | 9/2013 | Roy et al. |
| 9,116,105 B2 | 8/2015 | Veneruso et al. |
| 2002/0153897 A1* | 10/2002 | Evans ................ G01V 3/28 324/374 |
| 2002/0166699 A1* | 11/2002 | Evans ................ G01V 3/24 175/26 |
| 2003/0210061 A1 | 11/2003 | Fabris et al. |
| 2004/0104726 A1* | 6/2004 | Chemali ............ E21B 47/024 324/369 |
| 2008/0089005 A1* | 4/2008 | Choi ................ H01G 5/0132 361/278 |
| 2013/0231620 A1* | 9/2013 | Thirstrup ............ A61F 5/445 604/344 |
| 2015/0257923 A1* | 9/2015 | Thirstrup ............ A61F 13/02 604/318 |
| 2016/0003686 A1 | 1/2016 | Matsumoto et al. |

\* cited by examiner

A-A

PRODUCTION-LOGGING SENSOR

BACKGROUND

This invention pertains generally to technology for measuring the electrical capacitance and resistance characteristics of borehole fluids. More particularly, the invented technology relates to a single sensor probe that, when deployed in a borehole, provides for substantially simultaneous measurements of resistance and capacitance at substantially the same position in the borehole. Because the capacitance and resistance measurements are made with a single probe (the compound probe), the probe will occupy a smaller space than separate capacitance and resistance probes deployed to collect the same information. More compound probes than separate probes may be deployed in a given space. This allows for multiple probes to be simultaneously deployed in a small diameter borehole or tubular to provide measurements of fluid capacitance and resistance at various points at a given depth in the borehole. ("Depth" is used herein to denote the distance along the borehole from the surface. This may be different from "vertical depth" which denotes the distance at a particular point from the surface, regardless of the distance along the borehole. For example, different depths along a strictly horizontal portion of a wellbore will be at the same vertical depth.) Another advantage of the single-probe design is the elimination of the fluid droplets hanging in between the separate capacitance and resistance probes which will skew the measurements.

As is well known in the art, measures of resistance or capacitance of borehole fluids are useful for determining the type or mix of borehole fluids. For example, the resistance of the fluid (or, equivalently, the resistivity or conductivity) may provide information regarding the mix of hydrocarbon and brine. Similarly, the capacitance of the fluid (or the capacitive effect) may provide information regarding the type of fluid (e.g., oil, gas, water). Combining these measurements together provides more information. And combining these measurements with other borehole-fluid measurements (e.g., fluid density, fluid flow rate) can provide significant information about how a particular well is producing fluids.

Providing a number of resistance or capacitance measurements at the same depth provides information about fluid distribution in a cross section of the wellbore. Such an array measurement provides further information about how a particular well is producing fluids.

A borehole-fluid resistance or capacitance sensor typically includes a probe configured to be deployed in the fluid in the borehole and support electronics for acquiring the information from the probe. For example, a resistance sensor may include a probe comprising a source and a return electrode, electronics to drive a current from the source through the borehole fluid to the return, and electronics to measure the current and the voltage difference across the electrodes (which provides a measure of resistance of the fluids between the electrodes). A capacitance sensor may include a probe comprising two electrodes that are conductively isolated from each other and include a gap between for borehole fluid (thus forming a capacitor), electronics connected to the probe to drive an oscillation, and electronics to measure the frequency of the oscillation (which provides a measure of the capacitance, which is related to the relative permittivity of the borehole fluid).

The probe and support electronics for a borehole-fluid resistance or capacitance sensor take up space. The larger the sensors, the fewer sensors that can be deployed in the constrained space of the borehole. Accordingly, reducing the size of the sensors allows for deployment of more sensors in the borehole which increases the resolution of the resistance or capacitance measurement at a given depth. And using separate resistance and capacitance probes makes it difficult or impossible to measure both the resistance and the capacitance of the same quanta of fluid. Reducing probe size allows for closer spacing of diverse probe types. Combining resistance and capacitance probes into a single probe allows for a near simultaneous measurement of resistance and capacitance for a single fluid sample. The present invention is directed to reducing the sensor size and combining resistance and capacitance probes into a single compound probe.

SUMMARY

The present invention is directed to technology to satisfy the need for high-resolution measurements of the resistance and capacitance characteristics of fluids in a borehole.

In one aspect of the invention, a sensor includes three electrodes configured to form two electrode pairs each pair having a gap between the electrodes. One of the electrode pairs includes an electrically insulative layer disposed in the gap between the electrodes.

In another aspect of the invention, the sensor further includes a RC oscillator circuit in which the capacitance of the circuit is determined at least in part by the electrode pair with the electrically insulative layer disposed in the gap between the electrodes. The sensor may also include a counter (optionally implemented in hardware or software) to count the oscillations and thereby provide a measure of the frequency of the oscillation of the RC oscillator circuit and thereby provide a measure of the capacitance of the electrode pair with the electrically insulative layer disposed in the gap between the electrodes.

In another aspect of the invention, the sensor includes a source of electrical power (voltage and current) connected to one of the electrode pairs to provide a source of current through the gap between the electrodes when an electrically conductive material is disposed in the gap. The sensor may include a voltmeter to measure the voltage across the gap and a ammeter to measure the current flowing through the material in the gap and thereby provide a measure of the resistance of the material in the gap.

In another aspect of the invention, an electrode assembly including three electrodes configured to form two electrode pairs, each pair having a gap between the electrodes, is placed into a borehole containing borehole fluid such that the borehole fluid enters the gaps. A RC oscillator circuit is connected to the first electrode pair such that the electrode pair contributes to the capacitance of the circuit. A power supply is connected to the other electrode pair to provide voltage across that pair's gap and current through the borehole fluid in the gap. The frequency of the oscillation of the oscillator circuit is measured to provide a measure of the capacitance provided by the first electrode pair. The voltage across the other electrode's gap is measured and the current through the borehole fluid in the gap is measured to provide a measure of the borehole fluid's resistance.

BRIEF DESCRIPTION OF THE DRAWINGS

These and other features, aspects, and advantages of the present invention will become better understood with reference to the following description, appended claims, and accompanying drawings where:

DETAILED DESCRIPTION

Figure 1:
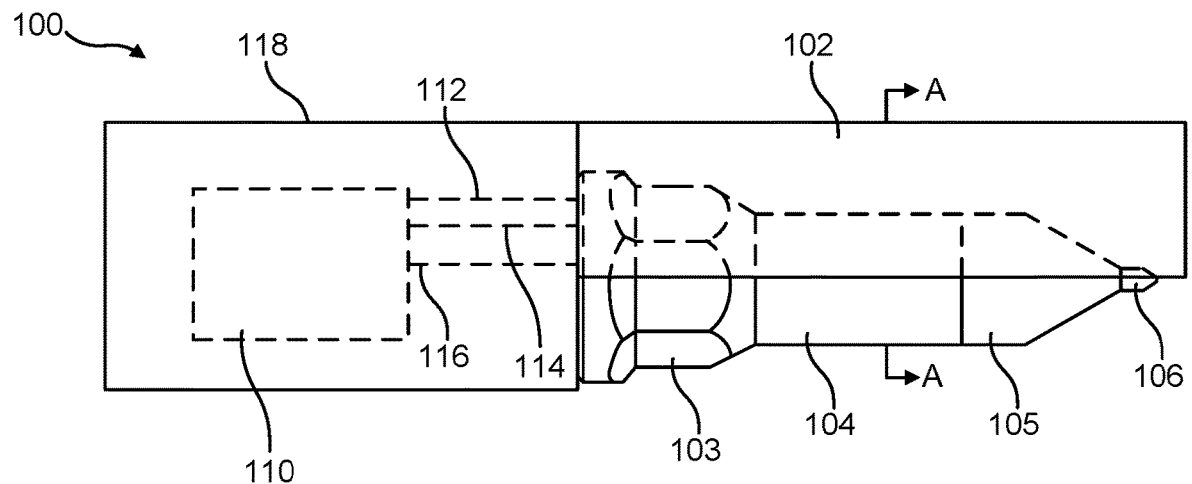
FIG. 1 is side view illustrating an exemplary borehole-fluid capacitance/resistance sensor according to an aspect of the invention.

In the summary above, and in the description below, reference is made to particular features of the invention in the context of exemplary embodiments of the invention. The features are described in the context of the exemplary embodiments to facilitate understanding. But the invention is not limited to the exemplary embodiments. And the features are not limited to the embodiments by which they are described. The invention provides a number of inventive features which can be combined in many ways, and the invention can be embodied in a wide variety of contexts. Unless expressly set forth as an essential feature of the invention, a feature of a particular embodiment should not be read into the claims unless expressly recited in a claim.

Except as explicitly defined otherwise, the words and phrases used herein, including terms used in the claims, carry the same meaning they carry to one of ordinary skill in the art as ordinarily used in the art.

Because one of ordinary skill in the art may best understand the structure of the invention by the function of various structural features of the invention, certain structural features may be explained or claimed with reference to the function of a feature. Unless used in the context of describing or claiming a particular inventive function (e.g., a process), reference to the function of a structural feature refers to the capability of the structural feature, not to an instance of use of the invention.

Except for claims that include language introducing a function with "means for" or "step for," the claims are not recited in so-called means-plus-function or step-plus-function format governed by 35 U.S.C. § 112(f). Claims that include the "means for [function]" language but also recite the structure for performing the function are not means-plus-function claims governed by § 112(f). Claims that include the "step for [function]" language but also recite an act for performing the function are not step-plus-function claims governed by § 112(f).

Except as otherwise stated herein or as is otherwise clear from context, the inventive methods comprising or consisting of more than one step may be carried out without concern for the order of the steps.

The terms "comprising," "comprises," "including," "includes," "having," "haves," and their grammatical equivalents are used herein to mean that other components or steps are optionally present. For example, an article comprising A, B, and C includes an article having only A, B, and C as well as articles having A, B, C, and other components. And a method comprising the steps A, B, and C includes methods having only the steps A, B, and C as well as methods having the steps A, B, C, and other steps.

Terms of degree, such as "substantially," "about," and "roughly" are used herein to denote features that satisfy their technological purpose equivalently to a feature that is "exact." For example, a component A is "substantially" perpendicular to a second component B if A and B are at an angle such as to equivalently satisfy the technological purpose of A being perpendicular to B.

Except as otherwise stated herein, or as is otherwise clear from context, the term "or" is used herein in its inclusive sense. For example, "A or B" means "A or B, or both A and B."

An exemplary borehole-fluid capacitance/resistance sensor 100 according to an aspect of the invention is depicted in FIG. 1. The dashed lines in the figure denote portions of items that would otherwise be hidden from view. The sensor includes a first electrode 102, a second electrode 104, and a third electrode 106. In combination, the three electrodes 102, 104, 106 form two electrode pairs. The first pair of electrodes comprises the first electrode 102 and the second electrode 104 with a gap between the electrodes 102, 104. An electrically insulating layer (not shown) is dispersed in the gap between the first electrode 102 and the second electrode 104 to prevent electrical-current conduction in the gap between the electrodes. For example, the second electrode 104 may be coated with nonconductive hydrophobic coating. The second pair of electrodes comprises the first electrode 102 and the third electrode 106 with a gap between the electrodes 102, 106. There is no electrical insulation dispersed in the gap between the first electrode 102 and the third electrode 106. Thus, if the gap is filled with an electrically conductive material, such as borehole fluid containing brine, electrical current may flow through the gap between the first and third electrodes 102, 106. A first electrically-insulating material 103 is placed between the first and second electrodes 102, 104. A second electrically-insulating material 105 is placed between the second and third electrodes 104, 106. The first and second insulating materials 103, 105 may be, for example, polyether ether ketone (PEEK).

The electrodes are electrically connected to an electronics section 110 located in a housing 118. The first electrode 102 is connected to the electronics section 110 through conductor 112. The second electrode 104 is connected to the electronics section 110 through conductor 114. The third electrode 106 is connected to the electronics section 110 through conductor 116. The first electrode 102 may be mechanically connected to the housing 118 or may be an integrally formed part of the housing 118. The first electrode 102 and the housing 118 may be electrically connected such that the housing is an electrical extension of the first electrode 102.

Figure 2:
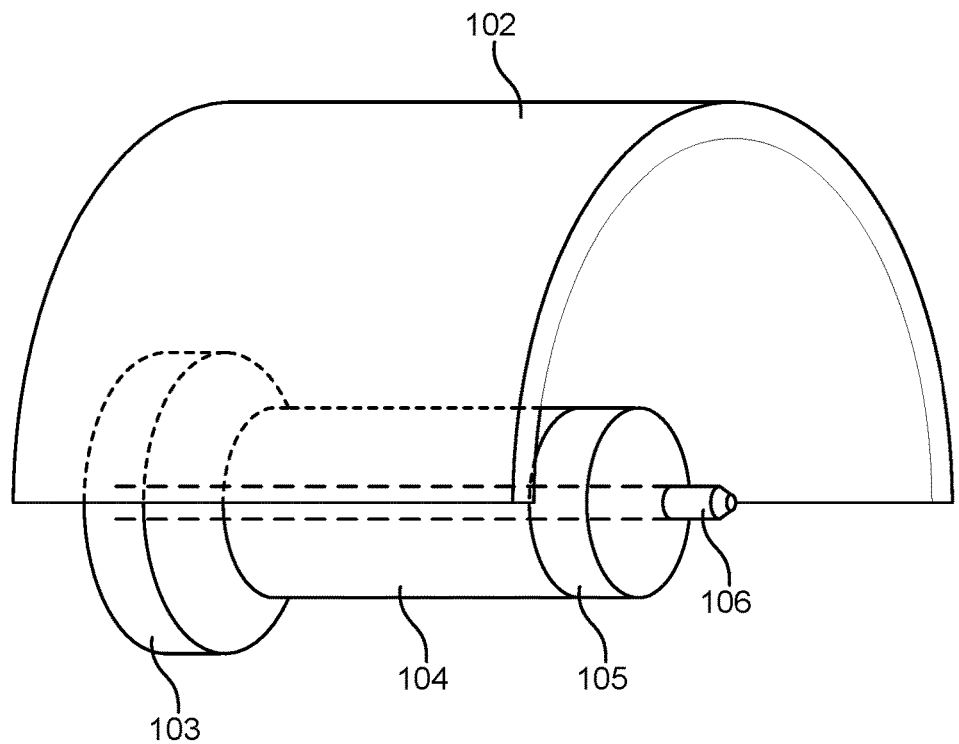
FIG. 2 is a perspective view illustrating an exemplary electrode assembly of an exemplary borehole-fluid capacitance/resistance sensor according to an aspect of the invention.

FIG. 2 is a perspective view of the electrode assembly of the exemplary borehole-fluid capacitance/resistance sensor 100. The dashed lines in the figure denote portions of items that would otherwise be hidden from view. As depicted in the figure, the first electrode 102 may partially envelop the second 104 and third 106 electrodes. The gap between the first electrode 102 and the second electrode 104 and the gap between the first electrode 102 and the third electrode 106 is configured to accept borehole fluid when the sensor 100 is deployed in a borehole.

Figure 3A:
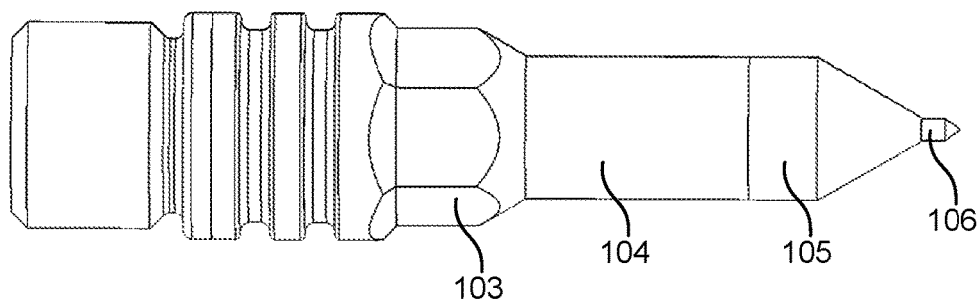
FIGS. 3A-3C are various views illustrating portions of an exemplary electrode assembly of an exemplary borehole-fluid capacitance/resistance sensor according to an aspect of the invention.
Figure 3B:
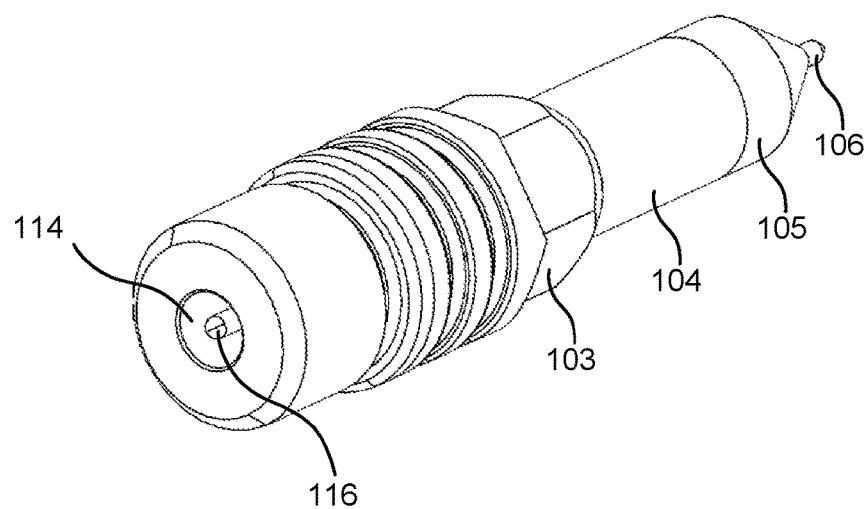
Figure 3C:
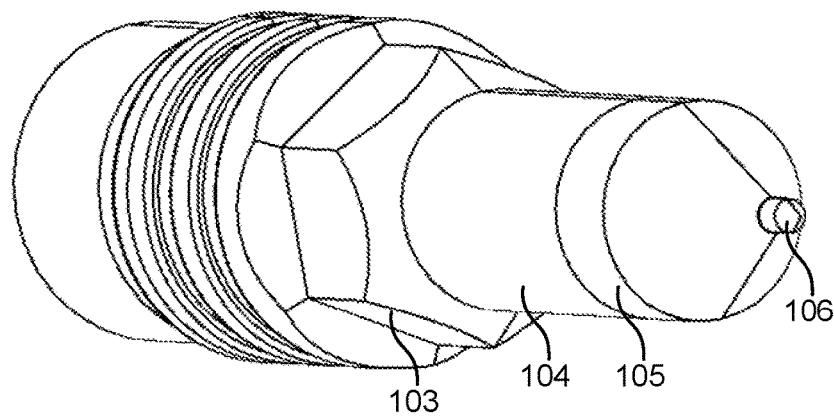

FIGS. 3A-3C depict various views of the portion of the exemplary electrode assembly comprising the second electrode 104 and the third electrode 106. FIG. 3A is a side view. FIG. 3B is a perspective view from the bottom of the assembly. ("Bottom" here refers to the end which connects to the housing 118 and electronics 110). FIG. 3C is a perspective view from the top of the assembly.

Figure 4:
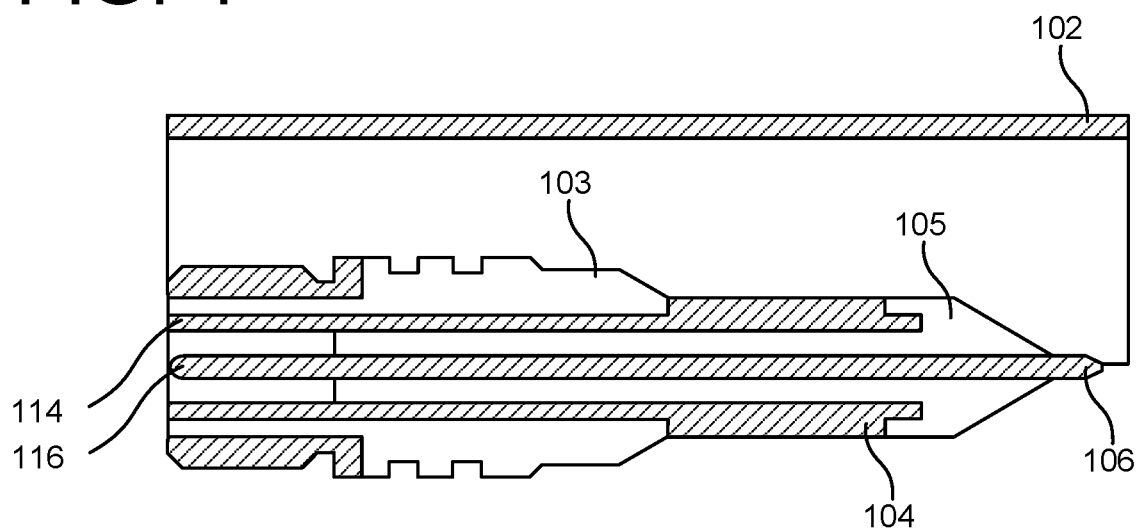
FIG. 4 is a side sectional view illustrating an exemplary electrode assembly of an exemplary borehole-fluid capacitance/resistance sensor according to an aspect of the invention.
Figure 5:
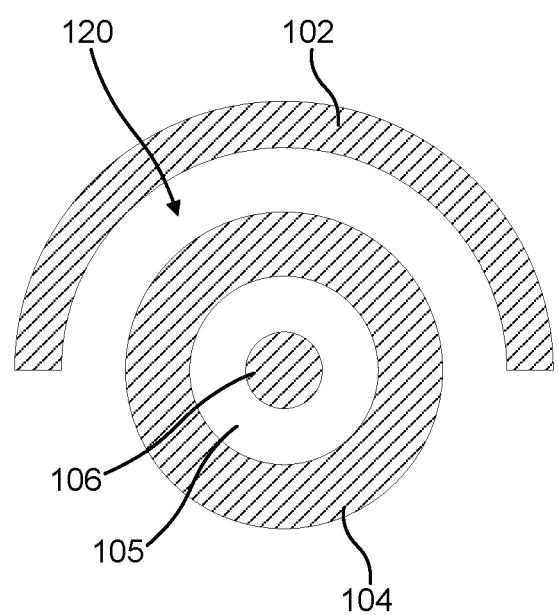
FIG. 5 is an end sectional view illustrating an exemplary electrode assembly of an exemplary borehole-fluid capacitance/resistance sensor according to an aspect of the invention.

FIGS. 4 and 5 are sectional views of the exemplary electrode assembly. FIG. 4 is a side sectional view with the electrodes 102, 104, 106 (along with an electrically-conductive threaded connector) denoted with diagonal hatching. For sake of clarity, only a portion of the first electrode 102 is denoted with hatching in FIG. 4. FIG. 5 is a top sectional view of section A-A in FIG. 1. The electrodes 102, 104, 106 are denoted with diagonal hatching in FIG. 5. The gap 120 between the first electrode 102 and the second and third electrodes 104, 106 is configured to accept borehole fluid when the sensor 100 is deployed in the borehole.

Figure 6:
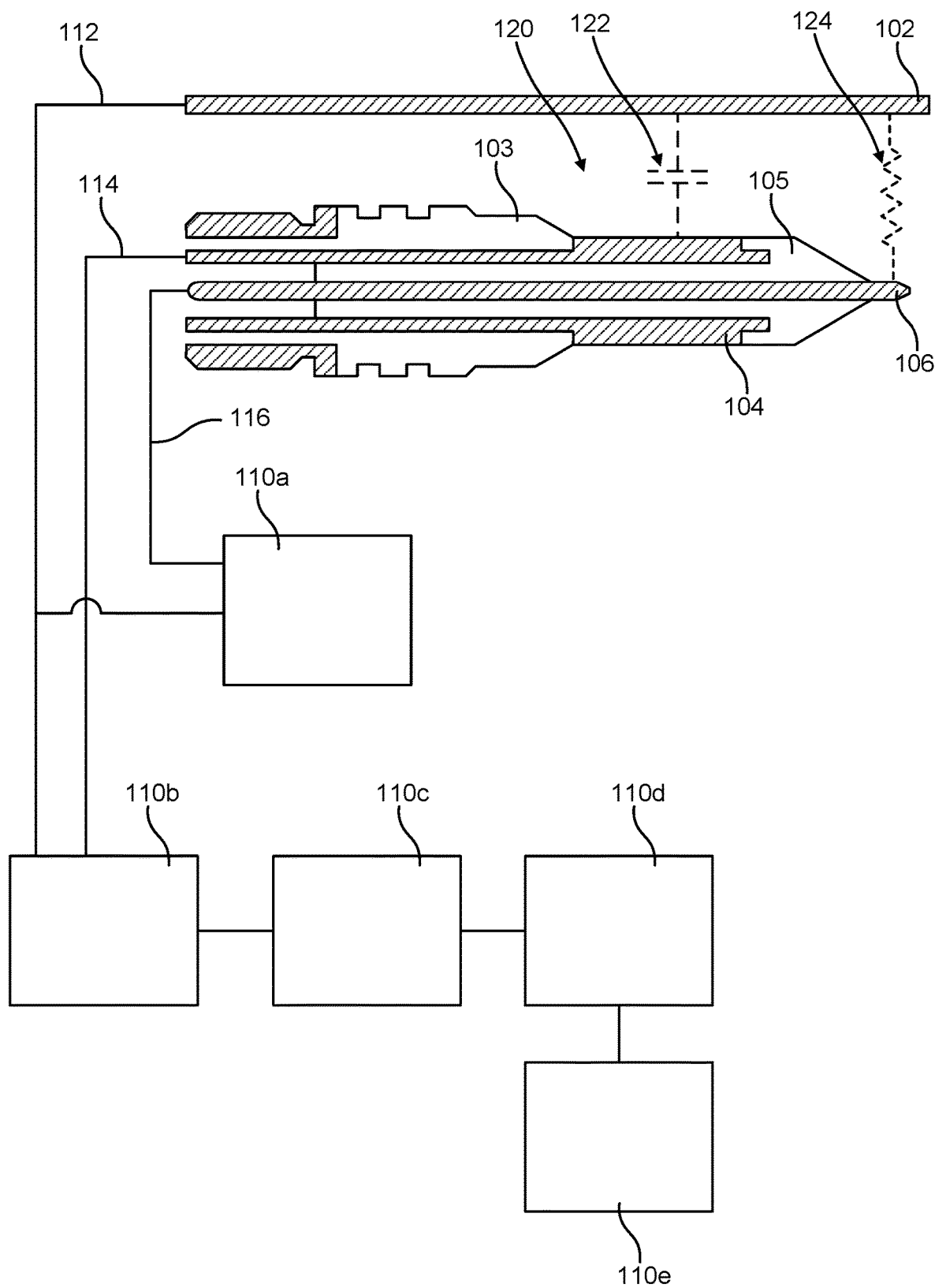
FIG. 6 is a block diagram illustrating the functional blocks of an exemplary borehole-fluid capacitance/resistance sensor according to an aspect of the invention.

FIG. 6 depicts a functional-block diagram of an exemplary sensor 100 deployed in borehole fluid. The electrode pair formed by the first electrode 102 and the second electrode 104 with borehole fluid present in the gap 120, forms a capacitance 122 between the first and second electrodes 102, 104 (with an electrically insulative layer, such as a coating on the second electrode 104, dispersed between the electrodes 102, 104). The electrode pair formed by the first electrode 102 and the third electrode 106 with borehole fluid present in the gap 120 forms a resistance 124 between the first and third electrodes 102, 106.

A precision-tuned local RC oscillator circuit 110b is connected to the capacitive electrode pair formed by the first electrode 102 and the second electrode 104. The output of the oscillator circuit is an oscillating signal (e.g., a square wave). The frequency of the circuit is a function of the capacitance 122 and thus a measure of the frequency provides a measure of the capacitance 122 (and thus of the permittivity of the borehole fluid). The oscillator 110b output may be processed by a low-pass filter 110c (perhaps with a Schmitt trigger) and provided to a microcontroller or other processor 110d that determines the oscillation frequency (e.g., by counting the square waves in a particular time period). (As is well known in the art, a counter may equivalently be implemented in hardware or software. For example, a counter may be implemented in a processor, it may be provided as a function-specific chip, or it may be implemented in a programmable logic circuit such as a field programmable gate array. The invention is not inherently limited to any particular counter.) In FIG. 6, the microcontroller 110d also receives temperature information from a temperature sensor such as a thermistor or resistance thermometer 110e. Positioning a temperature sensor 110e near the capacitive electrode pair allows for temperature compensation of the capacitance measure. For example, temperature information may be used to accurately compensate for the temperature drift of the RC oscillator circuit. Positioning the oscillator circuit 110b near the capacitive electrode pair reduces the effects of stray capacitance on the measurement.

A power supply (e.g., a source of known, though not necessarily predetermined, current and voltage) 110a is connected to the resistive electrode pair formed by the first electrode 102 and the third electrode 106. The relationship between current and voltage is a function of the resistance 124; thus, measures of current and voltage provide a measure of the resistance 124 (and thus of the resistivity of the borehole fluid).

The smaller the relative axial spacing of the second 104 and third 106 electrodes, the greater the overlap in the borehole fluid contributing to the capacitance 122 and that contributing to the resistance 124. ("Axial" is left-right in FIG. 6, the direction from the bottom to the top of the electrode assembly.) Thus, the sensor 100 can provide in-situ measurements of resistance and capacitance due to the borehole fluid at practically the same time for practically the same fluid.

Multiple electrode assemblies may be supported by a single electronics section through use of multiplexing. For example, a single power supply 110a may be selectively connected to one of multiple resistive electrode pairs through a multiplexer.

The resistance information provided by the power supply 110a and the capacitance information provided by the oscillator circuit 110b may be stored in memory or transmitted to a data-acquisition system through, e.g., wireline.

Figure 7:
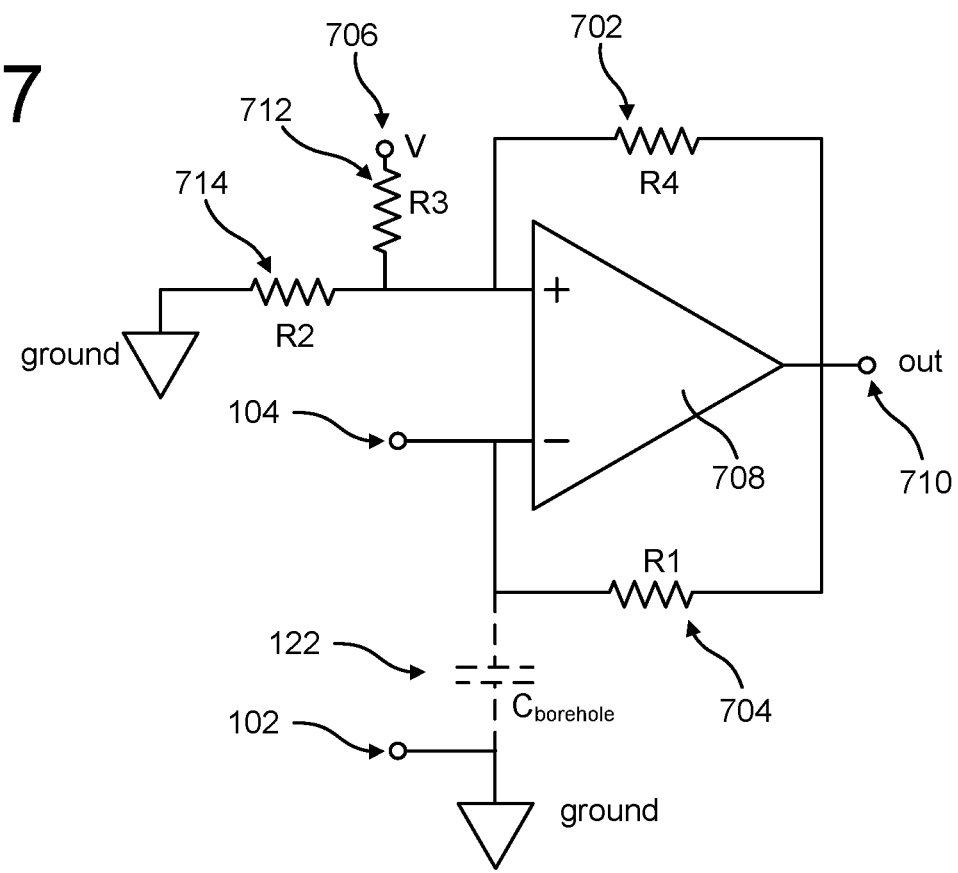
FIG. 7 is a schematic for an exemplary RC oscillator circuit of an exemplary borehole-fluid capacitance/resistance sensor according to an aspect of the invention.

An exemplary RC oscillator circuit is shown in FIG. 7. An input voltage 706 (e.g., 3.3V) is provided to the non-inverting input of an operational amplifier 708 through a resistor 712 of a known value R3. The second electrode 104 is electrically connected to the inverting input of the operational amplifier 708. The output 710 of the operational amplifier 708 (here, a comparator) is fed back to the non-inverting input through a resistor 702 of a known resistance R4. The output 710 of the operational amplifier is also fed back to the inverting input through another resister 704 of a known resistance R1. The first electrode 102 is connected to the circuit ground. The output 710 of the circuit provides a signal oscillating with a frequency that is a function of the capacitance 122 (provided here by the capacitive electrodes 102, 104 and borehole fluid) and the values (R1, R2, R3, R4) of the resistors 704, 714, 712, 702. The resistor values (R1, R2, R3, R4) are chosen to provide a measurable frequency change based on the range of expected capacitances. Thus, the circuit may be tuned for its intended environment. (The exemplary circuit is designed for a comparator running with a single supply. Equivalently, the comparator may run with a dual supply. For such a dual-supply configuration, the input voltage 706 and its connecting resistor 712 could be removed from the circuit.)

Measurement of the frequency of the oscillation of the output 710 signal provides a measure of the capacitance due to the borehole fluid. In practice, the RC oscillator circuit should be calibrated using capacitances of known value (as opposed to relying solely upon the analytical solution to the circuit to determine the capacitance).

Figure 8:
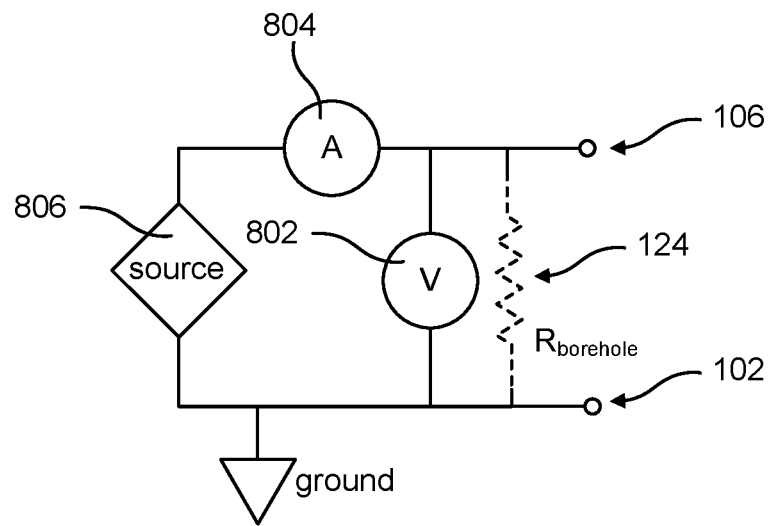
FIG. 8 is a schematic for an exemplary ohmmeter circuit of an exemplary borehole-fluid capacitance/resistance sensor according to an aspect of the invention

An exemplary circuit for determining the resistance of the borehole fluid disposed between the resistive electrode pair 102, 106 is shown in FIG. 8. A current/voltage source 806 provides current to the third electrode 106 which flows through the borehole fluid 124 to the first electrode 102 (shown here connected to circuit ground). A measure of current flowing through the borehole-fluid resistance 124 is provided with an ammeter 804 (which may be implemented in a variety of structural forms, as is well known in the art). A measure of voltage drop across the borehole-fluid resistance 124 is provided with a voltmeter 802 (which may be implemented in a variety of structural forms, as is well known in the art). The current and voltage measures provide a measure of borehole-fluid resistance 124. The power supply 806 may provide direct or alternating current.

While the foregoing description is directed to the preferred embodiments of the invention, other and further embodiments of the invention will be apparent to those skilled in the art and may be made without departing from the basic scope of the invention. And features described with reference to one embodiment may be combined with other embodiments, even if not explicitly stated above, without departing from the scope of the invention. The scope of the invention is defined by the claims which follow.

The invention claimed is:

1. A sensor comprising:
  (a) a first electrode;
  (b) a second electrode, positioned relative to the first electrode such as to define a first gap between the first electrode and the second electrode, wherein the first gap is configured to receive a fluid;
  (c) an electrically nonconductive layer placed between the first electrode and the second electrode such as to prevent an electrical current-path between the first electrode and second electrode from forming in the first gap, even if conductive fluid fills the first gap;
  (d) a third electrode, positioned relative to the first electrode such as to define a second gap between the first electrode and the third electrode, wherein an electrical current-path between the first electrode and third electrode is able to form in the second gap if conductive fluid fills the second gap; and
  (e) wherein the second electrode and the third electrode are electrically separated from each other with an electrically nonconductive material.

2. The sensor of claim 1 wherein the first gap is directly adjacent to the second gap.

3. The sensor of claim 1 wherein at least a portion of the second electrode defines a tube and the third electrode is at least partially disposed within the tube.

4. The sensor of claim 1 further comprising a voltage source connected to the first electrode and the third electrode.

5. The sensor of claim 1 further comprising a means for measuring a resistance of a fluid when the fluid is disposed in the second gap.

6. The sensor of claim 1 further comprising an RC oscillator circuit connected to the first electrode and the second electrode.

7. The sensor of claim 6 wherein the RC oscillator circuit is a relaxation oscillator.

8. The sensor of claim 6 further comprising a counter connected to the RC oscillator circuit.

9. The sensor of claim 1 further comprising a means for measuring a capacitance provided by the first electrode pair when a fluid is disposed in the first gap.

10. The sensor of claim 1 further comprising a temperature sensor.

11. The sensor of claim 1 further comprising:
  (a) an ohmmeter connected to the first and third electrodes such as to provide an indication of a resistance due to a fluid placed in the second gap; and
  (b) an RC oscillator circuit connected to the first and second electrodes such as to provide an indication of a capacitance due to a fluid placed in the first gap.

12. A method of measuring electrical characteristics of a borehole fluid, the method comprising:
  (a) disposing an electrode assembly in a fluid-containing borehole, the electrode assembly comprising:
    (i) a first electrode;
    (ii) a second electrode, positioned relative to the first electrode such as to define a first gap between the first electrode and the second electrode, wherein the first gap is configured to receive a fluid;
    (ii) an electrically nonconductive layer placed between the first electrode and the second electrode such as to prevent an electrical current-path between the first electrode and second electrode from forming in the first gap, even if conductive fluid is placed in the first gap;
    (iv) a third electrode, positioned relative to the first electrode such as to define a second gap between the first electrode and the third electrode, wherein an electrical current-path between the first electrode and third electrode is able to form in the second gap if conductive fluid is placed in the second gap; and
    (v) wherein the second electrode and the third electrode are electrically separated from each other with an electrically nonconductive material;
  (b) measuring a frequency of an oscillation of a RC oscillator circuit in which the first and second electrodes provide a capacitance within the circuit;
  (c) measuring a voltage between the first and third electrodes; and
  (d) measuring a current flowing between the first and third electrodes.

13. The method of claim 12 further comprising:
  (a) determining a resistance based on the voltage and current; and
  (b) determining a capacitance based on the frequency.

14. The method of claim 12 further comprising:
  (a) measuring a temperature;
  (b) determining a resistance based on the voltage and current and temperature; and
  (c) determining a capacitance based on the frequency and temperature.

* * * * *